United States Patent
Armstrong

(10) Patent No.: US 7,645,229 B2
(45) Date of Patent: Jan. 12, 2010

(54) INSTRUMENT AND METHOD FOR ENDOSCOPIC VISUALIZATION AND TREATMENT OF ANORECTAL FISTULA

(76) Inventor: David N. Armstrong, 1777 Brandon Hall Dr., Atlanta, GA (US) 30350

(*) Notice: Subject to any disclaimer, the term of this patent is extended or adjusted under 35 U.S.C. 154(b) by 473 days.

(21) Appl. No.: 10/945,634

(22) Filed: Sep. 21, 2004

(65) Prior Publication Data

US 2005/0070759 A1 Mar. 31, 2005

Related U.S. Application Data

(60) Provisional application No. 60/506,284, filed on Sep. 26, 2003, provisional application No. 60/538,365, filed on Jan. 21, 2004.

(51) Int. Cl.
*A61B 1/00* (2006.01)
(52) U.S. Cl. .............. 600/104; 600/101; 600/153; 600/155; 600/156; 600/160; 606/191; 606/197; 606/213; 623/1.1; 623/1.3; 623/1.31; 623/1.38
(58) Field of Classification Search .......... 606/191, 606/197, 213; 623/1.1–1.54; 600/101, 104, 600/153, 155–156, 160
See application file for complete search history.

(56) References Cited

U.S. PATENT DOCUMENTS

| 454,327 | A | * | 6/1891 | Brown ................ 606/145 |
| 2,127,903 | A | | 8/1938 | Bowen |
| 3,996,921 | A | | 12/1976 | Neuwirth ................ 128/2 |
| 4,511,653 | A | | 4/1985 | Play et al. |
| 4,902,508 | A | | 2/1990 | Badylak et al. |
| 4,956,178 | A | | 9/1990 | Badylak et al. |
| 5,192,302 | A | * | 3/1993 | Kensey et al. ............ 606/213 |
| 5,275,826 | A | | 1/1994 | Badylak et al. |
| 5,281,422 | A | | 1/1994 | Badylak et al. |
| 5,330,503 | A | | 7/1994 | Yoon |
| 5,345,948 | A | | 9/1994 | O'Donnell, Jr. ............ 128/898 |
| 5,374,261 | A | | 12/1994 | Yoon |
| RE34,866 | E | | 2/1995 | Kensey et al. |
| 5,514,158 | A | | 5/1996 | Kanesaka |
| 5,516,533 | A | | 5/1996 | Badylak et al. |
| 5,522,840 | A | | 6/1996 | Krajicek |

(Continued)

FOREIGN PATENT DOCUMENTS

EP 0 894 474 A1 2/1999

(Continued)

OTHER PUBLICATIONS https://ep.eur.nl/retrieve/2688/01.pdf#search='fistulotomy'. Schouten et al. Jul. 2001.*

(Continued)

*Primary Examiner*—Matthew J Kasztejna
(74) *Attorney, Agent, or Firm*—Brinks Hofer Gilson Lione

(57) ABSTRACT

A fiber-optic endoscopic instrument (Fistuloscope) is used to visualize anorectal fistula, and to accurately identify the course through the fistula. The instrument can be used to flush the fistula, to close the fistula tract by means of injecting sealants or placing grafts in the tract of the fistula or to pass setons, micro-instruments or other means to treat and seal the tract.

12 Claims, 2 Drawing Sheets

U.S. PATENT DOCUMENTS

| | | | |
|---|---|---|---|
| 5,554,389 A | 9/1996 | Badylak et al. | |
| 5,584,827 A | 12/1996 | Korteweg et al. | |
| 5,620,461 A | 4/1997 | Muijs Van De Moer | |
| 5,628,762 A | 5/1997 | Al-Tameem | 606/170 |
| 5,643,305 A | 7/1997 | Al-Tameem | 606/180 |
| 5,733,337 A | 3/1998 | Carr, Jr. et al. | |
| 5,752,974 A | 5/1998 | Rhee et al. | 606/214 |
| 5,755,791 A | 5/1998 | Whitson et al. | |
| 5,846,183 A | 12/1998 | Chilcoat | 600/136 |
| 5,860,978 A | 1/1999 | McDevitt et al. | |
| 5,947,994 A | 9/1999 | Louw et al. | 606/200 |
| 5,955,110 A | 9/1999 | Patel et al. | |
| 5,993,844 A | 11/1999 | Abraham et al. | |
| 5,997,575 A | 12/1999 | Whitson et al. | |
| 6,090,996 A | 7/2000 | Li | |
| 6,099,567 A | 8/2000 | Badylak et al. | |
| 6,149,581 A * | 11/2000 | Klingenstein | 600/114 |
| 6,270,515 B1 | 8/2001 | Linden | |
| 6,296,632 B1 | 10/2001 | Lüscher et al. | |
| 6,315,787 B1 * | 11/2001 | Tsugita et al. | 606/213 |
| 6,331,319 B1 | 12/2001 | Badylak et al. | |
| 6,475,232 B1 | 11/2002 | Babbs et al. | |
| 6,602,931 B2 | 8/2003 | Chen et al. | |
| 6,638,312 B2 | 10/2003 | Plouhar et al. | |
| 6,666,892 B2 | 12/2003 | Hiles | |
| 6,800,056 B2 * | 10/2004 | Tartaglia et al. | 600/114 |
| 7,485,087 B2 * | 2/2009 | Burgard | 600/32 |
| 2001/0039426 A1 * | 11/2001 | Makower et al. | 606/153 |
| 2003/0013989 A1 | 1/2003 | Obermiller et al. | |
| 2003/0051735 A1 | 3/2003 | Pavcnik et al. | |
| 2004/0064017 A1 * | 4/2004 | Cappiello et al. | 600/156 |
| 2005/0013844 A1 | 1/2005 | Hadlock et al. | |
| 2005/0049626 A1 | 3/2005 | Burgard | |
| 2005/0070759 A1 | 3/2005 | Armstrong | |
| 2005/0155608 A1 | 7/2005 | Pavcnik et al. | |
| 2005/0159776 A1 | 7/2005 | Armstrong | |
| 2005/0182495 A1 | 8/2005 | Perrone | |
| 2006/0015142 A1 | 1/2006 | Malazgirt | |
| 2006/0074447 A2 | 4/2006 | Armstrong | |

FOREIGN PATENT DOCUMENTS

| | | |
|---|---|---|
| RU | 2180529 | 8/1999 |
| SU | 1718837 | 3/1992 |
| WO | WO 93/16658 | 9/1993 |
| WO | WO 97/41778 | 11/1997 |
| WO | WO 98/25637 | 12/1997 |
| WO | WO 98/01088 | 1/1998 |
| WO | WO 98/22158 | 5/1998 |
| WO | WO/98/56290 | 12/1998 |
| WO | WO/00/45691 | 8/2000 |
| WO | WO 00/74576 A1 | 12/2000 |
| WO | WO 02/74192 A2 | 2/2002 |
| WO | WO 02/062234 A2 | 8/2002 |
| WO | WO 03/002165 | 1/2003 |
| WO | WO 2004/103187 | 12/2004 |
| WO | WO 2005/020823 | 3/2005 |
| WO | WO 2005/020847 | 3/2005 |
| WO | WO 2005/030035 | 4/2005 |
| WO | WO 2005/053617 A2 | 6/2005 |
| WO | WO 2005/070489 | 8/2005 |
| WO | WO 2006/119256 A | 11/2006 |
| WO | WO/2007/090155 | 8/2007 |

OTHER PUBLICATIONS

Athanasiadis S, Helmes C, Yazigi R, KÖhler A. The direct closure of the internal fistula opening without advancement flap for transsphincteric fistulas-in-ano. Dis Colon Rectum 2004;47:1174-80.

Excision of anal fistula with closure of the internal opening. Gustafsson U Dis Colon Rectum 2002;45:1672-1678.

Gordon N. Buchanan, M.Sc., F.R.C.S., Clive I. Bartram, F.R.C.R., Robin K.S. Phillips, M.S., F.R.C.S., Stuart W.T. Gould, M.S., F.R.C.S., Steve Halligan, M.D., F.R.C.R., Tim A. Rackall, M.D., F.R.C.S., Paul Sibbons, Ph.D., Richard G. Cohen, M.D., F.R.C.S., Efficacy of Fibrin Sealant in the Management of Complex Anal Fistula, Dis Colon Rectum, pp. 1167-1174, Sep. 2003.

Julio García-Aguilar, M.D., F.R.C.S., Cynthia S. Davey, M.S., Chap T. Le, Ph.D., Ann C. Lowry, M.D. and David A. Rothenberger, M.D., Patient satisfaction after surgical treatment for fistula-in-ano, Dis Colon Rectum, pp. 1206-1212, Sep. 2000.

Lindsey I, Smilgin-Humphreys MM, Cunningham C, Mortensen NJM, George B. A randomized, controlled trial of fibrin glue vs conventional treatment for anal fistula. Dis Colon Rectum 2002;45:1608-15.

Practice parameters for treatment of fistula in ano—Supporting documentation. The Standards Practice Task Force of the American Society of Colon and Rectal Surgeons, Dis Colon Rectum, pp. 1361.

Practice parameters for treatment of fistula in ano. The Standards Practice Task Force of the American Society of Colon and Rectal Surgeons, Dis Colon Rectum, pp. 1363-1372, Dec. 1996.

Sentovic Stephen M., Fibrin glue for anal fistulas. Dis Colon Rectum 2003;46:498-502.

David J. Schultz et al., "Procine Small Intestine Submucosa as a Treatment for Enterocutaneous Fistulas", J Am. Coll. Surg. pp. 541-543 (2002).

J. R. Miklos et al., "Rectovaginal Fistula Repair Utilizing a Cadaveric Dermal Allograft" Int. Urogynecol. J. 10: pp. 405-406 (1999).

Search Report for PCT/2006/045890.

Surgisis Anal Fistula Plug Nov. 30, 2005.

PCT/US2007/076656 International Search Report and Written Opinion.

* cited by examiner

POSTERIOR

ANTERIOR

INSTRUMENT AND METHOD FOR ENDOSCOPIC VISUALIZATION AND TREATMENT OF ANORECTAL FISTULA

CROSS REFERENCE

This application claims the benefit of Provisional Application No. 60/506,284 filed Sep. 26, 2003 and of Provisional Application No. 60/538,365, filed Jan. 21, 2004.

FIELD OF THE INVENTION

This invention concerns the treatment of anorectal fistulae of the human specie. A surgical instrument and procedure is used for endoscopically tracking and visualizing the internal aspect of an anorectal fistula, and for treating and closing the fistula tract, either surgically or by using a chemical sealant or a plug.

BACKGROUND OF THE INVENTION

Anorectal fistulae result from infection in the anal glands, which are located around the circumference of the distal anal canal that forms the anatomic landmark known as the dentate line. FIGS. 1 and 2 illustrate the typical anorectal fistulae 4 and 5 that commonly occur in man. The dentate line is shown at 1 of FIG. 1. Approximately 20-30 such glands are found in man. Infection in an anal gland usually results in an abscess, and the abscess then tracks through or around the sphincter muscles into the perianal skin, where it drains either spontaneously or surgically. The resulting tract is known as a fistula. The inner opening of the fistula, usually located at the dentate line, is known as the primary opening 2. The outer (external) opening, located in the perianal skin, is known as the secondary opening 3.

The path which these fistulae take, and their complexity, is very variable. A fistula may take a take a "straight line" path from the primary to the secondary opening, known as a simple fistula 4. Alternatively, the fistula may consist of multiple tracts ramifying from the internal (primary) opening and have multiple external (secondary) openings. This is known as a complex fistula 5.

The anatomic path which a fistula takes is classified according to its relationship to the anal sphincter muscles as shown in FIG. 1. The anal sphincter consists of two concentric bands of muscle, the inner or internal sphincter 6 and the outer or external anal sphincter 7. Fistulae which pass between the two concentric anal sphincters are known as inter-sphincteric fistulae 8. Those which pass through both internal and external sphincters are known as trans-sphincteric fistulae 9, and those which pass above both sphincters are called supra-sphincteric fistula 10. Fistulae resulting from Crohn's disease usually "ignore" these anatomic planes, and are known a "extra-anatomic" fistulae.

Many complex fistulae consist of multiple tracts, some blind-ending 11 and others leading to multiple external (secondary) openings 3. One of the most common complex fistulae is known as a horseshoe fistula 12, shown in FIG. 2. In this instance the infection starts in the anal gland (the primary opening) at the 12 o'clock location (with the patient in the prone position.) From this primary opening, fistulae pass bilaterally around the anal canal, in a circumferential manner. Multiple external (secondary) openings from a horseshoe fistula may occur anywhere around the periphery of the anal canal, resulting in a fistula tract with a characteristic horseshoe configuration 12.

Failed surgical treatment leads to potential complications such as incontinence and multiple complex fistula formation. Alternative methods and instruments have been described such as a coring-out instrument by U.S. Pat. No. 5,628,762 and U.S. Pat. No. 5,643,305; however, this tends to make the fistula wider and more difficult to close.

A prior art technique for treating a perianal fistulae was to make an incision adjacent the anus until the incision contacts the fistula and then excise the fistula from the anal tissue. This surgical procedure tends to sever the fibers of the anal sphincter, and may cause incontinence.

Other surgical treatment of fistulae traditionally involved passing a fistula probe through the tract of the fistula in a blind manner, using primarily only tactile sensation and experience to guide to probe. Having passed the probe through the fistula tract, the overlying tissue is surgically divided. This is known as a fistulotomy. Since a variable amount of sphincter muscle is divided during the procedure, fistulotomy also may result in impaired sphincter control, and even frank incontinence.

Alternatively, the fistula tract may be surgically drained by inserting a narrow diameter rubber drain through the tract. This is known as a seton (Greek, "thread"). The seton is passed through the fistula tract and tied as a loop around the contained tissue and left for several weeks or months, prior to definitive closure or sealing of the fistula. This procedure is usually performed to drain infection from the area, and to mature the fistula tract prior to a definitive closure procedure.

More recently, methods have evolved to inject sclerosant or sealant (collagen or fibrin glue) into the tract of the fistula to block the fistula. Such sealants are described in prior art, such as Rhee U.S. Pat. No. 5,752,974. One drawback with prior art is these glues are very viscous and clog the narrow-bore channels of the instrument as described in the current invention. Closure of a fistula using a sealant is usually performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

Whatever method is used, accurate identification of the entire course of the fistula tract usually is a prerequisite for successful surgery. Traditionally the course of the fistula tract is determined by using a long, thin, metal probe (a fistula probe). The probe is passed into the external opening and maneuvered in a blind manner through the fistula tract, and out through the internal (primary) opening. Since the probe is passed in a blind manner, there is a hazard of "missing" the actual fistula tract, and creating additional tracts. This results in creating further fistulae, "false passages", incorrect location of the primary opening, and persistent or recurrent fistula formation. Surgical treatment of fistulae is often problematic, and recurrence rates of up 30% are described. Surgical fistulotomy of horseshoe fistulae results in an incontinence rate in up to 60% of patients, because of the need to divide sphincter muscle during surgery. Even use of fibrin glues is associated with high recurrence rates. There are reports of failure rates of over 80% in "blind" injection of sealant into a complex fistula, generally due to the presence of unrecognized tracts and infection within the fistula tract.

An important step in successful closure of a fistula tract is accurate identification and closure of the primary opening of the fistula. Once the internal opening has been accurately identified, effective closure is necessary to prevents recurrence.

This invention is concerned with an improved process of identifying the fistula tract, treating the tract and closing the tract.

SUMMARY OF THE INVENTION

This invention concerns an improved treatment of anorectal fistula of humans. More particularly, the invention includes a method and an instrument to accurately identify the course of an anorectal fistula tract by endoscopic visualization of the fistula tract. The passing of the endoscope along a fistula tract under direct visualization reduces the likelihood of creating false passages and facilitates more accurate identification of the entire fistula tract. In addition, the instrument in this procedure allows for more accurate placement of setons, provides a means to clean the fistula tract, and allows more precise injection of sealants or placement of occlusive plugs in the tract to successfully close the tract.

DETAILED DESCRIPTION

Figure 1:
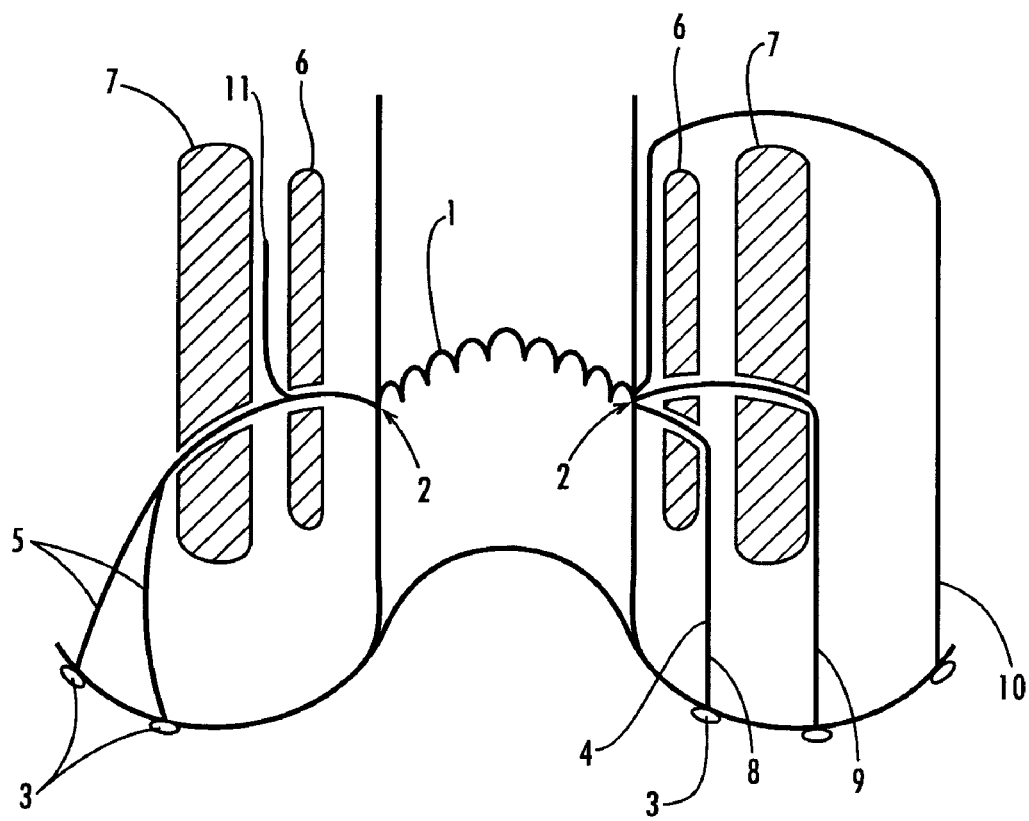
FIG. 1 is a schematic illustration of a typical human body showing the sphincter mussels and the possible anatomic courses of various forms of anorectal fistula (longitudinal plane).
Figure 2:
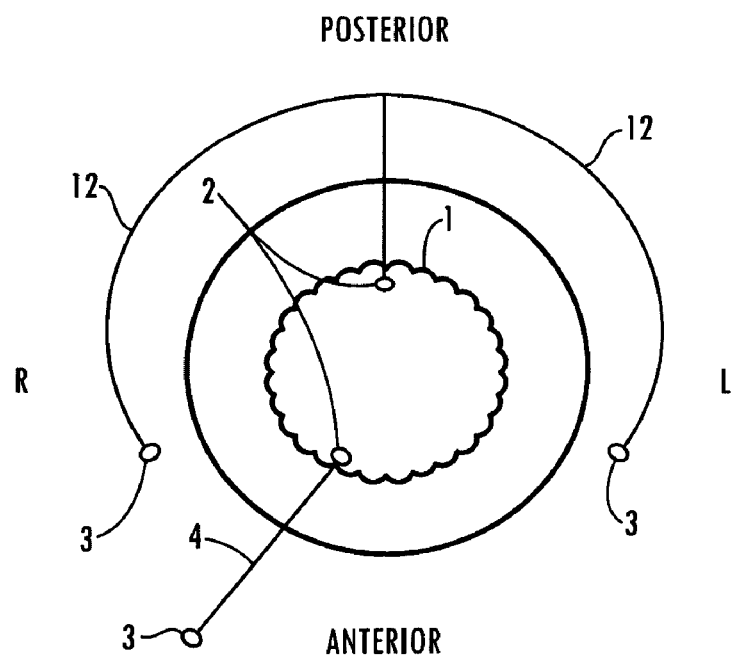
FIG. 2 is a schematic illustration of a posterior of a typical human body showing the possible simple anorectal fistula and horse-shoe fistula (perineal view).
Figure 3:
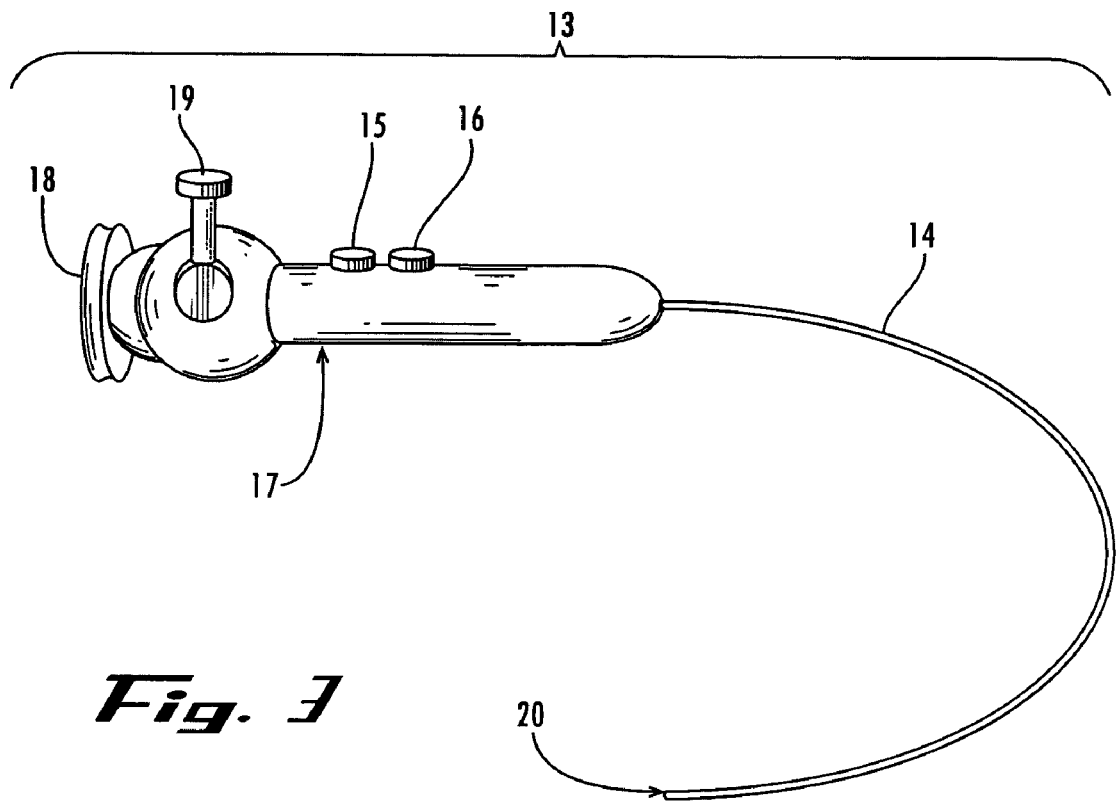
FIG. 3 is a schematic diagram of a flexible fiber-optic endoscope, (Fistuloscope) used for visualizing and treating anorectal fistula.

Referring in more detail to the drawings, the instrument 15, designated as the Fistuloscope, includes a fiber-optic endoscopic device, for the visualization of anorectal fistulae. The endoscope includes a head assembly 17, a probe or probe 14 and a tip 20. The probe is approximately 6-12 inches long, with a typical outside diameter of 0.5 to 3.0 mm and a tapered tip that may be used to perform the visualization and treatment of an anorectal fistula: The endoscope system includes in its probe 14 fiber-optic bundles for visualization and illumination, an irrigation port 15 and channel for ante-grade irrigation of fluid, and an instrument port 16 and channel for the passage of guide-wires, drains, instruments or solutions such as sealants or sclerosants. The head assembly 17 includes an optical viewing and lens system that may be attached to a video camera, a video monitor and a video recorder for ease of viewing at the distal end or tip of the instrument. The head assembly also incorporates a high intensity light source, and a lever system to steer the endoscope.

The tip 20 of the endoscope may be tapered to facilitate insertion into the external opening of a perianal fistula. The endoscope is passed under direct visualization into the secondary opening, through the entire length of the fistula, and out through the internal (primary) opening. The probe 14 of the endoscope possesses appropriate physical properties to allow the endoscope to be passed through the narrow fistula tract without buckling or kinking, and to be capable of being directed or steered in the appropriate direction. The probe of the endoscope may be rigid, malleable, semi-flexible or flexible. In an alternative embodiment of the current invention, only the leading tip 20 of the endoscope is flexible or directable, to permit the endoscope to be turned or become angulated as its distal or leading end is advanced along the duct of the fistula, along the curved path of the fistula duct.

Since the typical fistula is very narrow and may angulate sharply or curve abruptly as a horseshoe fistula, the endoscope usually must be directed or steered through the fistula tract. This requires some degree of ante-grade force to be applied to the instrument. The probe of the endoscope therefore possesses the required stiffness to allow adequate force to be applied to the instrument without it buckling or kinking.

The probe of the endoscope incorporates multiple optical fibers, enclosed within a suitable protective sheath or cladding. Several differing types of optical fibers and protective sheaths may be used, depending on the desired physical properties of the endoscope. The properties of the probe 14 of the endoscope may be rigid, malleable, semi-flexible, or flexible. Optical fibers used in rigid endoscopes generally consist of glass fibers made of silicone, silicone dioxide or suitable equivalent. Since a single optical fiber usually cannot transmit an image and only transmit light of a given intensity and color, multiple optical fibers (an optical bundle) are used for image transmission. Clarity and definition of the image is dependant upon the diameter and number of optical fibers in the optical bundle. In addition, each individual optical fiber must maintain its correct relationship with neighboring fibers, at both the proximal and distal ends of the endoscope, for a true likeness of the image to be transmitted through the bundle. This constant relationship of optical fibers is known as "coherent transmission". Non-aligned or random distribution of the optical fibers is referred to as "incoherent transmission" and is generally used only as a means of light transmission, to illuminate the endoscopic field. In a rigid endoscope, the optical fibers may be protected by a crush resistant coat of surgical steel or suitable alloy, to avoid damage to the delicate optical fibers.

Semi-flexible or malleable endoscopes utilize non-rigid optical fibers, manufactured from a silica polymer (such as Borosilicate) or a plastic polymer, (such as Polymethylmethacrylate (PMMA)). Coherent silica-based or plastic-based optical fibers have the required characteristics for image resolution, and have the added advantage of being flexible or malleable. In addition, individual silica- or plastic polymer fibers can be manufactured at extremely small diameters, and the resulting endoscopes can be as small as 0.2-0.5 mm diameter. These endoscopes form the class of "ultra-thin" endoscopes, used clinically to gain access to blood vessels (angioscopes) as described in U.S. Pat. No. 5,947,994, very small ducts such lachrymal ducts as described in U.S. Pat. No. 5,345,948, or to visualize the interior of an organ such as the uterus, as described in U.S. Pat. No. 3,996,921. Alternatively, "ultra-thin" endoscopes can be configured as malleable "needle scopes", which may be introduced into the peritoneal cavity to perform "mini-laparoscopy" of the abdomen, for example to look for bleeding after abdominal trauma. These silica or hydrocarbon-based fibers are also more durable than rigid glass fibers, and better withstand the wear and tear of clinical use. Semi-flexible or malleable endoscopes are generally clad in a crush-resistant sheath, to protect the optical fibers, yet provide the required degree of flexibility and rigidity. Such protective sheaths generally consist of either a flexible woven metallic or alloy sheath, a flexible spirally-configured metallic or alloy sheath, or a flexible plastic compound. The type of sheath utilized is determined by the requisite degree of flexibility and rigidity required for each class of endoscope to perform a particular clinical purpose.

Protective cladding about the probe of flexible endoscopes usually are of flexible plastic sheaths, with appropriate stiffness according to the desired physical properties.

Endoscopes may also utilize a CD chip to acquire a digital image, rather than transmit images via coherent optical fibers. These CD chips such as the CCD (Charged Coupled Device), convert an optical image (i.e. a light pattern) to an electronic image (an electric charge pattern). Such mini-CCD chips are well known in the digital camcorder industry, and will not be elaborated on further. One or more mini-CCD chips are mounted on the very tip of the endoscope, and the resulting electronic image is transmitted to a suitable output device such as a video monitor or CD/DVD recorder. This configuration of often referred to as the "chip-on-a-stick" configuration. By avoiding optical fibers, these "digital endoscopes" are very durable, and produce very high-resolution images. By positioning the chips at the tip of the endoscope, the resulting endoscope may have a wide variety of flexion capabilities, such as 3D omni-directional, or 360 degree flexion, without the risk of cracking or breaking the traditional optical fibers, as in conventional endoscopes.

Each class of endoscope (rigid, malleable, semi-flexible and flexible endoscopes) may be coated with a final outer coating of latex or other water-proofing material to render the final endoscope waterproof, or a low-friction coating to facilitate passage through a fistula tract.

In addition the endoscope possesses a means to allow the operator to direct or steer the endoscope through the twists and turns of the fistula tract. This is provided by means of a flexible and steerable endoscope, wherein either the probe or the tip is directable in one, two or three planes.

In the flexible version of the instrument, the endoscope may be angulated in any plane or direction, to permit the scope to be directed along the fistula tract. Directional capability in flexible endoscopes is provided by means of pull strings attached to the tip 20 or probe 14 of the endoscope, and connected to levers 19 in the head assembly. This configuration is often referred to as "cable-and-lever" mechanism, and is well known in prior art. An example of a steerable probe is disclosed in U.S. Pat. No. 5,846,183, which is incorporated herein by reference. The levers such as 18 and 19 can be used to control the probe.

In the semi-flexible option of the instrument, the probe possesses more stiffness than conventional flexible endoscopes. This would allow the instrument to be passed through the fistula tract under the required amount of ante-grade force, without buckling or kinking due to excessive flexibility.

In the rigid version of the endoscope, the probe is configured in a straight line, for use in simple or straight fistulae. Alternatively, the probe may be configured in a curvilinear or "hockey stick" shape. This shape allows easy passage of the probe up either limb of a "horseshoe fistula" 12, and the bend at the tip of the "hockey stick" allows easy exit of the instrument out of the primary opening in the posterior midline of the anal canal 2. In the malleable version of the instrument, the probe is composed of a malleable material such as a woven or spirally-configured metallic or alloy sheath, or a plastic (hydrocarbon-based) material, which may be bent to the necessary angle or curvature, to allow passage through the fistula tract. The shape of the endoscope probe may be altered sequentially as the instrument is passed further and further into the fistula tract, until the primary opening is identified. This is the traditional method of exploring fistula tracts using conventional "blind" fistula probes.

In an alternative embodiment, only the tip of the endoscope 20 may be directable, to allow passage through the fistula tract. The tip may be directable in one, two or three planes by means of pull strings and levers 19 as described in prior art. See U.S. Pat. No. 5,846,183. In this embodiment, the probe 14 of the instrument may be rigid, malleable or semi-flexible, whilst the tip alone is flexible or otherwise directable. This embodiment incorporates the necessary rigidity in the probe of the instrument, and the required flexibility in the tip, to allow for tip to be steered or directed in the appropriate direction. The relatively rigid probe may be fabricated of a tubular metallic or alloy sheath, and the relatively flexible tip fabricated of a woven, or spirally-configured metallic or alloy sheath, or a plastic (hydrocarbon-based) sheath.

In an alternative embodiment, the tip 20 of the instruction is movable in only one plane, using a pivot or articulating mechanism in the tip of the endoscope. In the latter embodiment, the tip may be angulated in one plane, through 0-360 degrees. This ability to deflect the tip up to 360 degrees, combined with twisting or torquing the endoscope probe, enables the instrument to be directed in three planes thus allowing the tip of the endoscope to be directed in the appropriate direction.

In a preferred embodiment of the invention, the tip 20 of the endoscope is tapered to approximately 0.1 mm to 2.0 mm to allow the instrument to be inserted into the fistula tract more easily.

To provide the adequate means of visualization of the fistula tract, the instrument also incorporates a high intensity light source, such as fiber-optic bundles for illumination, and may also include a lens for a video camera, monitor or other means of displaying the images in real time and recording the images. The use of light sources and fiber-optic bundles is well described in prior art in instruments such as gastroscopes, colonoscopes, and bronchoscopes. Illumination of the field of view is provided by fiber-optic bundles, which transmit light from a high intensity light source to the field of view. Other imaging fiber-optic bundles transmit images for the field of view to the head assembly of the endoscope.

A lens system in the head assembly may magnify the views provided by imaging fiber-optic bundles. These images may be conveyed by a video camera assembly, connected to the head assembly of the endoscope and displayed real time on a video output monitor. The fiber-optic bundles, lens systems and camera/video features are well described in prior art and can be used to facilitate real-time visualization of the fistula tract. Alternatively, the image may be transmitted from the tip of the endoscope electronically by means of one or more CCD chips, located in the tip of the endoscope, and transmitted to a monitor or suitable viewing device.

To obtain adequate views through the endoscope in the very tight confines of the fistula tract, it may be necessary to infuse a clear fluid medium through the endoscope, as the instrument is passed along the fistula tract. The clear irrigation fluid usually expands the fistula tract ahead of the advancing scopes and usually provides much better and clearer visualization. In addition, the infusion of fluid into the tract irrigates out necrotic and inflammatory tissue, which would otherwise result in infection of sealant material. The liquid or irrigation fluid is infused in an ante-grade manner via an irrigation port 15 in the head assembly of the scope. This leads to the irrigation channel, which terminates in the tip of the instrument 20. The fluid is infused from and external bag of fluid and connected to the port of the irrigation channel by means of flexible tubing. If necessary, the fluid is infused under pressure using a pressure bag applied to the fluid source, to increase the pressure under which the infusion is infused.

In order to pass guide-wires or micro-instruments into the fistula, an instrument channel runs through the probe of the instrument. The instrument channel is accessed via an instrument port 16 in the head of the instrument and exits in the tip of the endoscope. The instrument channel is used for passing guide-wires, drains, micro-instruments or for injection of sealants or placement of occlusive plugs. In one embodiment, one common channel serves as both an irrigation and instrument channel. This common channel is accessed via irrigation/instrument ports 15, 16.

Closure of a fistula tract may be performed as a one-stage or two-stage procedure. As a one-stage procedure, the fistula tract is closed or sealed at the same time at the initial surgery. The advantage of this method is that it is avoids a second operation and minimizes expense and inconvenience. The main disadvantage is that immediate injection of the sealant into an "unprepared" and possibly infected fistula tract may result in secondary infection of the sealant material. By using the current method of endoscopic visualization and irrigation of the fistula, the tract is "cleaned out" by means of the irrigating fluid. Any inflammatory or necrotic tissue within the tract is therefore removed prior to injecting a sealant. As an alternative embodiment, antibiotics can be utilized in the irrigation fluid, as an extra precaution or means of treating any residual infection within the fistula.

As a two-stage procedure, a seton is first placed through the fistula tract, to allow mechanical drainage of the fistula tract. This can be followed several weeks later by removal of the seton and injection of the sealant into the fistula.

It usually is desirable to close the tract of the fistula after any preliminary treatment. One closure procedure is the injection of a sealant in the tract. The channel through the shaft 14 of the instrument can be used to inject a sealant or sclerosing solution into the fistula tract or any side branches of the main fistula tract. Several possible sealants are described in prior art. One of the more commonly used is fibrin glue, known as Tisseal (Baxter Inc). The glue is prepared by mixing coagulation activation factors with fibrinogen, which react to form fibrin. The fibrin forms a matrix, which acts as a "scaffold" for tissue in-growth, with resulting sealing of the fistula tract. This may be preformed as a one-stage procedure, after first cleaning out the fistula tract by irrigation as described above. Alternatively, fibrin sealant may be performed as a two-stage procedure: After first placing a seton in the tract, several weeks later the second stage procedure is performed when the seton is removed, and the sealant is injected in to the fistula tract.

One drawback to the use of Tisseal is the very thick and viscous nature of the fibrin, which can permanently block the very narrow channel of the instrument. Alternatively, a thinner and less viscous sealant may be used to seal the fistula tract. This involves the use of an autologous composite of platelets and growth factors (Symphony PCS, DePuy AcroMed Inc), derived from the patient's own blood. The composite is derived from a fresh sample of blood, which is drawn from the patient at the time of surgery. The blood is centrifuged, and the platelets, which contain growth factors such as EGF and TGFβ are harvested. Having centrifuged the blood retrieved the platelet "pellet" and prepared the composite, the sealant is injected into the fistula tracts through the instrument channel. Since this is performed under direct vision, all the fistula tracts can be individually sealed, with a lower incidence of "missed fistula" and thus a higher success rate. Again, injection of thinner sealants such as Symphony can be performed as a one-stage or two-stage procedure. Prior irrigation and cleaning of the fistula tract allows for safer and more successful one-stage procedure, than was previously possible.

Treatment of a complex anorectal fistula using the current instrument and method would involve the following steps: The tip 20 of the instrument is inserted into the external (secondary) opening 3 of the fistula tract and advanced under direct vision through the entire length of the tract and out through the internal (primary) opening 2. This is made possible by viewing a video monitor, which provides real-time views of the internal anatomy of the fistula tract. Having identified the entire length of the fistula tract, it may be either closed at that time (one-stage) or a seton passed, and closed several weeks later (two-stage procedure). In order to place a seton, either the endoscope or a guide-wire is passed through internal opening 2. A drain or seton is then attached to the guide-wire or endoscope, and pulled retrograde through the fistula tract, and tied as a loop around the contained tissue. Any extensions of the fistula from the main tract are identified and a seton passed through each tract. In so doing, all extensions from the main fistula tract are accurately identified and treated appropriately.

In the second procedure, definitive closure of the fistula tract is performed. To accomplish this, each seton is removed, and sealant is injected into each tract, using the fistuloscope. In an alternative embodiment, other sealants such as soft tissue grafts (Surgisis, Wilson Cook Medical Inc); antibiotic beads (Septopal, Biomet Orthopedics Inc); Topical thrombin (FloSeal, Fusion Medical Technologies Inc; Gelatin sponge, Pharmacia and Upjohn Inc; JMI, Jones Pharmacia Inc); autologous platelet rich plasma; or other sealant material can be inserted into the tract under direct vision. The sealant blocks or closes the tract of the fistula. Alternatively, micro-instruments such as surgical clips, plugs or screws can be used to close the fistula tract. The method and instrument described allows a safer and more successful treatment of anorectal fistula, and the avoidance of potentially serious complications.

Figure 4:
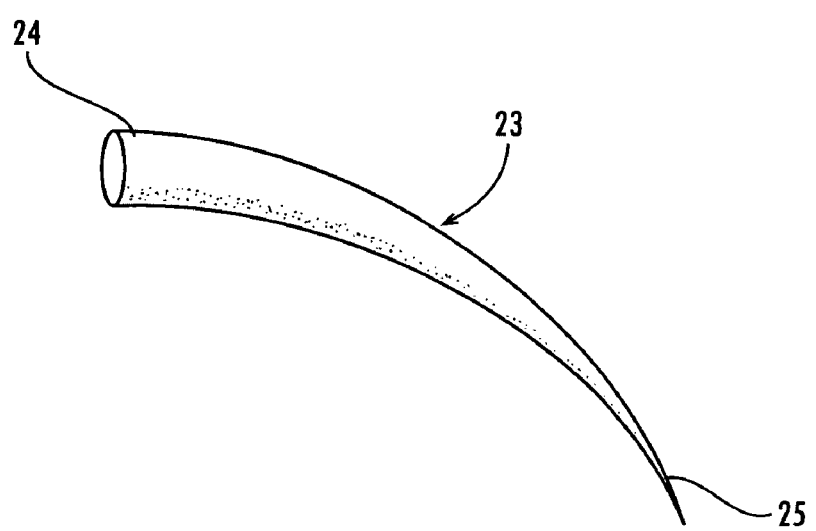
FIG. 4 is a tapered plug used for closing the tract of a fistula.

The instrument also can be used to place a plug in the primary opening of the tract of the fistula. As shown in FIG. 4, a tapering fistula graft 23 can be used for occlusion of the anorectal fistula. The graft has a tapering cord configuration and comprises a "trumpeted" head end 24, which tapers gradually to a filamentous tail 25. The graft is made of absorbable biological or synthetic material. The fistula graft is two to four inches long, and the diameter of the head is from five to ten millimeters and tapers to a diameter of one to two millimeters at its tail. The graft can be made of biological materials that include tissue from the patient (an Autograft), tissue from a human cadaveric donor (Allograft), or tissue from an unrelated animal donor (Xenograft). Potential Allograft tissue can be drawn from a skin biopsy of the patient. Once the fibroblasts have regenerated and formed enough new tissue, the new tissue is injected back into the surgical site of the same patient. This takes several weeks to complete, but tissue rejection and disease transmission are reduced with this procedure. One such product is Isolagen (Isolagen, Inc.). Suitable cadaveric Allografts include AlloDerm (LifeCell Corp.), Cymetra (LifeCell Corp.), Dermaloga, Fascion (Fascia Biosystems, Inc.), and Suspend (Mentor). These products are freeze-dried, or lyophilized, acellular dermal tissue from cadaveric donors. Some require reconstitution before implantation. Disease transmission or antigenic reaction can occur, but the risk of these reactions are minimized by the extensive screening and processing of the material. Xenograft materials include Surgisis (Cook Surgical), Permacol (TSL Inc.), Pelvicol (Bard Inc.) and Peri-Guard (Bio-Vascular Inc.). Biological material has been rendered non-cellular during processing to avoid immunological rejection. The collagenous tissue frame of the material remains intact, to allow for in-growth of host cells, and eventual incorporation into the host tissue itself. The biological tissues may be implanted in potentially infected surgical fields, and resist infection, unlike non-absorbable synthetic preparations, which may elicit a foreign body reaction, or act as a nidus for infection.

Potential synthetic absorbable materials include Polyglactin, Polydioxanone, Hyaluronic acid, and Polyglycolic acid. These materials avoid foreign body rejection, which is seen with non-absorbable materials, and are eventually incorporated into the host tissue. Each of these biological and synthetic materials elicit little immunological reaction and have variable degrees of resistance to infection. The biological and synthetic absorbable grafts are therefore incorporated into the host tissues of fistula tract, thereby occluding the fistula tract.

The graft is inserted into the fistula tract by pulling the graft tail first through the primary opening, toward the secondary opening. This can be accomplished using a pair of surgical hemostats, or a fistula probe, which is passed through the outer (secondary) opening and out through the primary opening. The tail of the graft is then grasped by the hemostats, or secured to the probe, and the graft is withdrawn retrograde into the fistula tract. As the graft is withdrawn through the tract, the "trumpeted" head end of the graft is gradually "wedged" into the primary opening, in the manner of inserting a plug in a hole. As the head becomes wedged into the primary opening, the graft becomes lodged in place, does not fall out or exude as with the fibrin glue technique. The head and/or tail can be further secured by sutures and trimmed to avoid either end protruding excessively after the procedure. By virtue of the trumpeted head of the graft, it can be used for any diameter of primary opening, and by applying adequate traction to the graft during insertion, the head of the graft conforms exactly to the size of the primary opening. Any size of primary opening can be closed with the current invention, up to the limits of the head diameter.

For multiple fistula, multiple grafts can be inserted, until all fistula tracts have been addressed. In the case of complex fistula, for instance the horse-shoe fistula, there may be one primary opening and two or more tracts leading from that opening. In this instance a graft may be configured with one head component and two tails. Each "tail" is withdrawn through the primary opening into each fistula in turn, and sufficient traction applied to wedge the head component snugly into the primary opening. Each of the tails and the head of the graft are secured by sutures, if necessary, and excess graft is trimmed.

An alternative methodology involves preliminary endoscopic visualization (fistuloscopy) and cleaning of the fistula tract. This is performed by a very thin flexible endoscope, which is inserted into the secondary opening of the fistula tract and advanced under direct vision through the fistula tract and out through the primary opening. By performing preliminary fistuloscopy of the fistula tracts, the primary opening is accurately identified and the tracts are "cleaned out" by means of the irrigating fluid. Any inflammatory or necrotic tissue within the tract is therefore removed, prior to inserting the graft. The tail of the graft may be attached to the fistuloscope, which is then withdrawn through the fistula tract, and the graft is wedged in place as described above.

As an alternative embodiment, antibiotics can be incorporated into the graft as an extra precaution or means of treating any residual infection within the fistula. The graft can also be used in conjunction with a sealant or sclerosing solution which is injected into the fistula tract or any side branches of the main fistula tract. Several possible sealants are described in prior art. One of the more commonly used is fibrin glue, known as Tisseal (Baxter Inc.). The glue is prepared by mixing coagulation activation factors with fibrinogen, which react to form fibrin. The fibrin forms a matrix which acts as a "scaffold" for tissue in-growth, with resulting sealing of the fistula tract.

Alternatively, autologous fibrin glue can be used in conjunction with the fistula graft in order to supplement the adhesive and occlusive properties of the method. This involves the use of an autologous composite of platelets and growth factors (Symphony PCS, DePuy AcroMed, Inc), derived from the patient's own blood. The composite is derived from a fresh sample of blood, which is drawn from the patient at the time of surgery. The blood is centrifuged and the platelets, which contain growth factors such as EGF and TBFβ are harvested. Having centrigued the blood, retrieved the platelet pellet and prepared the composite, the sealant is injected into the fistula tracts to help maintain the graft in place.

In the event that multiple fistula are present, a fistula graft can be inserted into each fistula tract, until all the primary openings have been closed. Accurate identification of all fistula tracts is made technically easier and more accurate by first performing fistuloscopy, whereby each fistula tract is identified and the primary opening is accurately identified. Once the entire tract has been identified and cleaned out, the graft is pulled tail-first through the primary opening toward the secondary opening, using the fistuloscope or an instrument passed through the instrument channel of the scope. Adequate traction is applied to the tail to ensure that the trumpeted head of the graft is firmly secured in the primary opening. This maintains the graft in place, ensures a perfect seal of the primary opening and thereby prevents recurrence of the fistula. The graft may be secured with additional sutures at the primary and/or secondary opening, and the graft is trimmed to remove redundant graft from protruding from the fistula tract.

The above method and invention describes a new technique of minimally invasive fistula closure. The technique obviates the need for surgical fistulotomy, avoids surgical pain and the attendant complications of the procedure. In addition it provides accurate and complete closure of the primary opening, so preventing a recurrent or persistent fistula. The technique involves no cutting of tissue, sphincter damage is prevented, and incontinence is eliminated.

Although preferred embodiments of the invention has been disclosed in detail herein, it will be obvious to those skilled in the art that variations and modifications of the disclosed embodiments can be made without departing from the spirit and scope of the invention as set forth in the following claims.

I claim:

1. A method of surgically treating an anorectal fistula having a tract with a primary opening and a secondary opening, comprising:
   inserting the distal end of an elongated probe having a tubular passage extending along its length into the secondary opening of the tract of the fistula, wherein the elongated probe allows for endoscopic visualization of the tract of the fistula,
   cleaning the tract of the fistula with an irrigating fluid,
   advancing the distal end of the probe progressively through the tract of the fistula through the primary opening of the tract of the fistula,
   positioning a plug near the primary opening, wherein the primary opening is near the dentate line in the anal canal,
   attaching the distal end of the probe extending from the primary opening of the fistula tract to the plug, and
   drawing the plug with the probe into blocking relationship in the primary opening of the tract of the fistula, whereby the plug is wedged into the primary opening.

2. The method of claim 1 wherein the plug is an elongated plug tapered along its length with a first end of enlarged breadth and a second end of smaller breadth,
- wherein attaching the probe to the plug comprises attaching the probe to the smaller end of the plug, and
- wherein drawing the plug with the probe into blocking relationship in the primary end of the tract of the fistula comprises drawing the end of smaller breadth of the plug into the primary end of the tract of the fistula.

3. The method of claim 2, and further comprising trimming a portion of the plug protruding from the primary end of the tract of the fistula.

4. The method of claim 1, wherein the plug is a graft comprising material absorbable by the human body.

5. The method of claim 1, wherein the plug comprises a xenograft material.

6. The method of claim 5, wherein the xenograft material comprises a material in which a collagenous tissue frame remains intact to allow for in-growth of host cells and eventual incorporation of the material into host tissue.

7. The method of claim 1, wherein the plug comprises acellular dermal tissue.

8. A method of surgically treating an anorectal fistula having a tract with a primary opening and a secondary opening, comprising:
- inserting a distal end of an elongated probe having a tubular passage extending along its length into the secondary opening of the tract of the fistula, wherein the elongated probe allows for endoscopic visualization of the tract of the fistula and for cleaning the tract of the fistula with an irrigating fluid,
- advancing the distal end of the probe progressively through the tract of the fistula through the primary opening of the tract of the fistula,
- positioning a plug consisting of a xenograft material or an allograft material near the primary opening, wherein the primary opening is near the dentate line in the anal canal,
- attaching the probe extending from the primary opening of the fistula tract to the plug, and
- drawing the plug into blocking relationship in the primary opening of the tract of the fistula, whereby the plug is wedged into the primary opening.

9. The method of claim 8 wherein providing a plug comprises providing an elongated plug tapered along its length with a first end of enlarged breadth and a second end of smaller breadth,
- wherein attaching the probe to the plug comprises attaching the probe to the smaller end of the plug, and
- wherein drawing the plug with the probe into blocking relationship in the primary end of the tract of the fistula comprises drawing the end of smaller breadth of the plug into the primary end of the tract of the fistula.

10. The method of claim 8, wherein the plug is a graft comprising material absorbable by the human body.

11. The method of claim 8, and further including trimming a portion of the plug protruding from the primary end of the tract of the fistula.

12. The method of claim 8, wherein the plug is a graft made from acellular dermal tissue.

* * * * *

UNITED STATES PATENT AND TRADEMARK OFFICE
CERTIFICATE OF CORRECTION

PATENT NO. : 7,645,229 B2 Page 1 of 1
APPLICATION NO. : 10/945634
DATED : January 12, 2010
INVENTOR(S) : David N. Armstrong It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 472 days.

Signed and Sealed this

Sixteenth Day of November, 2010

David J. Kappos
*Director of the United States Patent and Trademark Office*